United States Patent [19]

Proni

[11] Patent Number: 5,738,334
[45] Date of Patent: *Apr. 14, 1998

[54] DIAPHRAGM FLOW CONTROL ASSEMBLY

[75] Inventor: Oscar Proni, Hollywood, Fla.

[73] Assignee: Safegrip Inc., Tequesta, Fla.

[*] Notice: The term of this patent shall not extend beyond the expiration date of Pat. No. 5,580,030.

[21] Appl. No.: 644,864

[22] Filed: May 10, 1996

Related U.S. Application Data

[63] Continuation-in-part of Ser. No. 139,126, Oct. 21, 1993, Pat. No. 5,580,030.
[51] Int. Cl.$^6$ .................................................... F16L 37/28
[52] U.S. Cl. .......................... 251/149.1; 604/256; 604/283; 604/905
[58] Field of Search ........................ 251/149.1, 149.7, 251/331; 604/256, 905, 244, 283

[56] References Cited

U.S. PATENT DOCUMENTS

| | | | |
|---|---|---|---|
| 4,946,133 | 8/1990 | Johnson et al. | 251/149.1 |
| 5,221,272 | 6/1993 | Proni | 604/283 |
| 5,580,030 | 12/1996 | Proni | 604/256 X |

*Primary Examiner*—Kevin Lee
*Attorney, Agent, or Firm*—Morrison & Foerster LLP

[57] ABSTRACT

A diaphragm fluid flow control assembly serving to provide a leak-proof seal for fluid-containing structures and serving to provide a leak-proof seal while fluid is extracted from the structures via a blunt tipped tube or needle. A perforation in the diaphragm is sealed closed by compressive forces within the diaphragm prior to insertion of a needle through the diaphragm into a fluid containing structure such as an intravenous bag, a syringe or medicament bottle. The diaphragm is also sealed after removal of the blunt tipped needle from the diaphragm. While the blunt tipped needle is inserted through the diaphragm and fluid is extracted from a fluid-containing structure, the diaphragm is in sealing engagement with the external surface of the inserted needle thereby allowing fluid to be removed from the container through the needle and preserving the sterility of the fluid. The assembly serves as a sterilization preserving transmission valve and cap for fluids stored in containers commonly used in the medical and health care field.

11 Claims, 12 Drawing Sheets

DIAPHRAGM FLOW CONTROL ASSEMBLY

REFERENCE TO RELATED APPLICATION

This application is a continuation-in-part of Ser. No. 08/139,126, filed Oct. 21, 1993, U.S. Pat. No. 5,580,030.

BACKGROUND OF THE INVENTION

1. Field of the Invention

This invention relates to a diaphragm fluid flow control assembly which seals against fluid leakage prior to insertion of, during insertion and while inserted, and after removal of a hollow blunt plastic tube or needle.

2. Discussion of the Related Art

Storing fluids in sterile containers and extracting fluids from containers while maintaining sterility of the fluids is an important part of the physician's and medical staff's treatment of patients. Traditionally, sharp pointed objects such as needles have served in the extraction of fluids. Recently, there has been much concern in the medical field of inadvertent pricking or puncturing of both patients and medical staff. Recently, various locking mechanisms and devices containing protected or enclosed sharp needles have been developed. The focus of these products has been the mechanical locking means.

The vast majority of these devices uses sharp-tipped needles. There has been relatively little attention paid to the use of blunt or moderately sharp needles. To use a blunt needle, a pre-pierced or perforated seal is required.

Presently, a seal consisting of an extended gum rubber plug which fits into and is compressed by the walls of a hollow tube is available. A portion of the plug may be formed so as to fit around the end of the hollow tube. This plug is bulky and derives compressive forces to close the central hole by being squeezed upon insertion into the tube. However, to utilize this seal, the user must simultaneously hold open a lock mechanism while forcing a blunt plastic tube through an extended length of the tube occupied by the gum rubber seal. The extended length of this seal requires significant force to push a blunt tube or needle through it.

SUMMARY OF THE INVENTION

This invention overcomes the disadvantages of the conventional diaphragms presently available. With the diaphragm of this invention, during the entire time the tube is inserted, the diaphragm is in sealing engagement with the external surface of the tube while free flow of a liquid occurs within the hollow tube. The diaphragm functions as a seal for containers used typically in medical applications such as bottles, syringes and intravenous bags. These containers may be loaded with quantities of fluids which are extracted upon penetration of the diaphragm. The diaphragm serves as a leak-proof seal which maintains the sterility of the fluid-containing container yet permits easy removal of a desired quantity of fluid while maintaining sterility of the fluid contents during extraction. The diaphragm assembly may be combined effectively as a component of a fluid control or transfer system when a separate mechanical locking mechanism is utilized which locks a device, containing the tube to be inserted through the diaphragm, with the fluid containing structure within which the diaphragm is mounted.

It is a feature of this invention to provide a self-sealing, fluid-tight, perforated diaphragm easily penetrable by a moderately sharp or blunt-ended plastic tube or needle so as to form a fluid-tight seal with the tube or needle when inserted through the diaphragm. For the purposes of this invention a tube or needle is blunt-tipped when the plane of the opening in the tube or needle is substantially at a 90° angle to the outer surface of the tube or needle.

Another feature of the invention is to provide a self-sealing perforated diaphragm such that after removal of the tube or needle inserted through the diaphragm, the diaphragm will close and form a fluid-tight seal.

Yet another feature of the invention is to provide a self-sealing, penetrable and reusable diaphragm assembly to serve as a cap to retain fluid within medicament bottles, pre-loaded syringes, intravenous bags and the like.

A further feature of the invention is to provide a self-sealing and reusable diaphragm assembly and conduit serving as the female insert to mate and lock with a quick-connect fluid coupling assembly serving as the basic building block in a unified system for fluid transmission in the medical and health care fields.

These and other features and advantages of the invention are provided by a diaphragm assembly comprising a perforated circular disk of rubber or other suitable material; a plastic conduit or tube-segment having an internal surface with a circumferential shoulder or step; and a pressing ring fitting into the plastic conduit or tube-segment, holding the circular disk within the tube, squeezing the circular disk against the internal shoulder of the conduit and creating compressive forces directed inward toward the central axis of the conduit to form a fluid-tight seal.

Preferably, the compressive forces created when the pressing ring squeezes the edges of the perforated circular disk against the internal shoulder of the conduit deform the circular disk into a dome or cupola form having a concave side and a convex side so that the disk is sealed against flow of liquid from the conduit volume bordering the convex side of the disk to the tube volume bordering the concave side of the disk.

It is preferred that the difference between the inner and outer diameters of the pressing ring is greater than the distance from the inner surface of the plastic conduit to the end of the shoulder or step measured along a line normal to the inner surface of the conduit.

The diaphragm preferably mates and locks within a quick-connect coupling assembly. The coupling assembly comprises a primary body including a centrally disposed elongated channel extending therethrough coaxially to the longitudinal axis thereof, a non-flexible central portion, a flexible retaining portion and a portion integrally joining the non-flexible portion to the flexible portion; and a diaphragm piercing or puncturing blunt, cylindrically shaped hollow needle incorporated within and coaxial to the longitudinal axis of the primary body having the exterior surface of the needle integrally attached to the surface of the non-flexible portion of the primary body having the exterior surface of the needle integrally attached to the surface of the non-flexible portion of the primary body and extending longitudinally beyond the non-flexible portion a sufficient length so as to terminate within the flexible portion of the primary body.

By using the diaphragm assembly of this invention it is possible to construct a fully assembled unified fluid system in which all ports of the system are the ports of this invention or a combination of the port of this invention and other conventional ports, depending on the applications to which the system is put.

BRIEF DESCRIPTION OF THE DRAWINGS

The above objects and features of the present invention will be apparent to those skilled in the art from the following description of the preferred embodiments thereof when considered in conjunction with the appended drawings in which:

FIGS. 23 (a) and 23(b) depict a snap-on end cap in partially engaged and engaged positions, respectively, on the end of a conduit according to this invention.

DETAILED DESCRIPTION OF THE INVENTION

Figure 1:
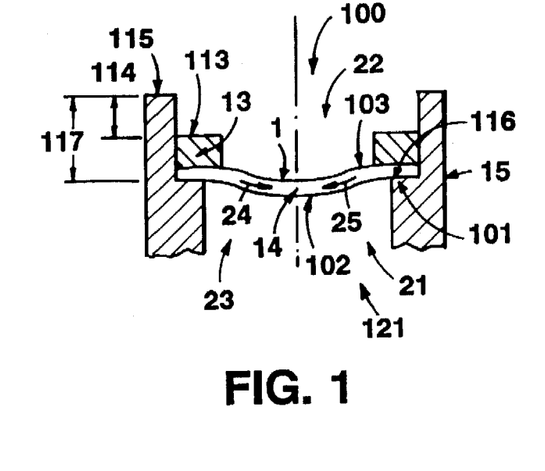
FIG. 1 illustrates a cut-away side view of the diaphragm assembly according to the invention.
Figure 2:
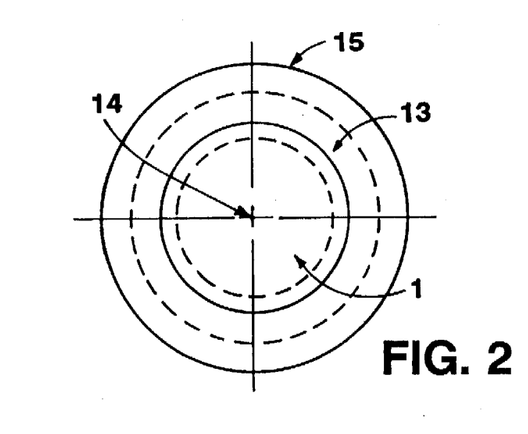
FIG. 2 illustrates a concave side end view of the diaphragm assembly according to FIG. 1.
Figure 3:
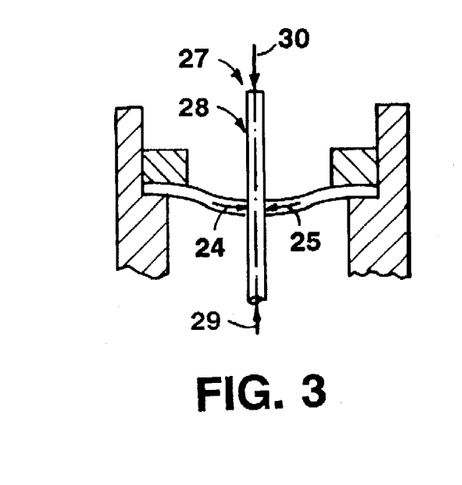
FIG. 3 illustrates a cut-away side view of the diaphragm assembly in the engaged position.

Referring to FIGS. 1 and 3, the complete diaphragm assembly 100 is shown in a cross sectional side view, comprising a cupola or dome-shaped diaphragm 1 having a perforation 14, a pressing or retaining ring 13, and a plastic conduit 15, having an elongated channel 121 centrally disposed along a longitudinal axis and having an inner-surface circumferential shoulder or step 101, encircling the longitudinal axis. A top view of diaphragm assembly 100, as seen looking toward concave surface 103 of diaphragm 1 is shown in FIG. 2.

FIG. 3 shows diaphragm 1 and retaining ring 13 mounted within conduit 15 in an engaged position with a blunt plastic needle or conduit 27. FIG. 1 shows the diaphragm assembly in the unengaged or rest position, either prior to insertion of conduit 27, or after removal of conduit 27. The diaphragm 1 has a convex surface 102, a concave surface 103 and is held in position within conduit 15 between pressing or retaining ring 13 and tube shoulder 101.

Diaphragm 1 divides the space within conduit 15 into the two volumes 22 and 21, with volume 21 adjoining convex diaphragm surface 102 and volume 22 adjoining concave diaphragm surface 103. The front surface 113 of retaining ring 13 is placed a distance 114 from the proximal end 115 of tube 15. The front surface 116 of shoulder 101 is located at a distance 117 from tube end 115.

Figure 5A:
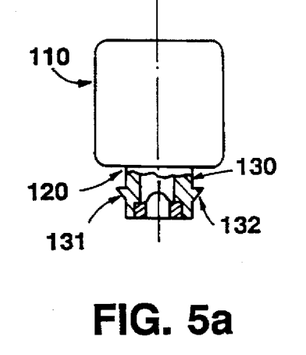
FIG. 5(a) illustrates a view of the diaphragm assembly as part of an intravenous bag.
Figure 5B:
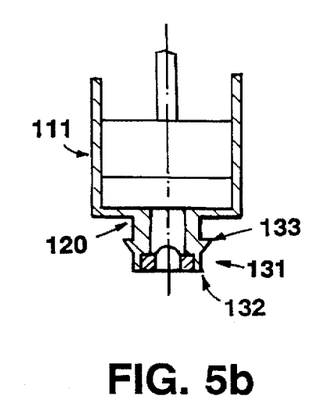
FIG. 5(b) illustrates the diaphragm assembly as part of a syringe.
Figure 5C:
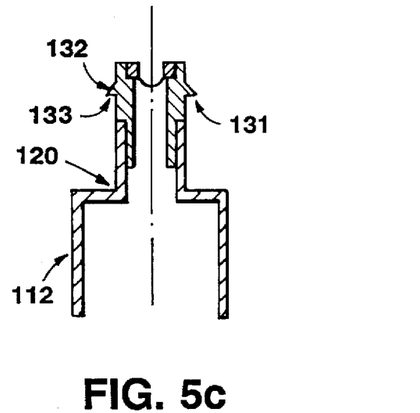
FIG. 5(c) illustrates the diaphragm assembly as part of a medicament bottle.

Referring to FIG. 5, tube or conduit 15 is shown having a distal end 120 opening into a fluid container or reservoir in the form of an intravenous bag 110, syringe 111, or medicament bottle 112.

Compressive forces 24 and 25 exist within diaphragm 1 and serve to seal perforation 14 in the absence of a conduit, to form a fluid-tight seal with the outer surface of conduit 27 and to form diaphragm 1 into a dome shape with concave surface 103 and convex surface 102. The forces 24 and 25 are created when ring 13 is pressed into tube 15 trapping and squeezing diaphragm 1 around the periphery against front surface 116 of internal shoulder 101 of conduit 15. Perforation 14 may be in the form of a straight line cut, two crossing straight line cuts, circular or any of various suitable geometric shapes. The maximum dimension of perforation 14 is normally slightly less than the outer diameter of any tube or conduit 27, but may be of any size so as to form a leak-proof seal about the external surface of the conduit 27.

Figure 4:
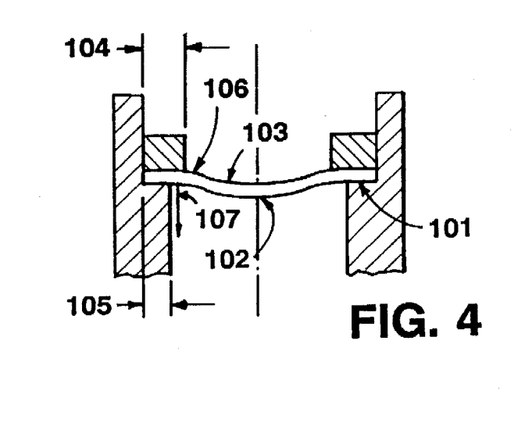
FIG. 4 illustrates a detail of the ring, diaphragm, and shoulder common contact region.

Referring to FIG. 4, the radial width of pressing ring 13, is shown as 104, and the radial width of shoulder 101 is shown as 105. Ring radial width 104 exceeds shoulder radial width 105. When latex, rubber, elastomer, thermoplastic elastomer or any other suitable material for diaphragm 1 seeks to expand against the squeezing of ring 13, it can expand only in region 106, in which the shoulder 101, is not present. Expansion in direction 107 forms diaphragm 1 into a dome-shaped surface and which creates compressive forces 24 and 25.

Prior to being squeezed between ring 13 and shoulder 101, diaphragm 1 is in the form of a perforated circular disk contained essentially in a plane. The squeezing by ring 13 of diaphragm 1 against front surface 116 of shoulder 101 causes the diaphragm to change shape from a circular disk to a circular dome-shape having a concave surface 103 and a convex surface 102.

Penetration of diaphragm 1 is made by moving blunt conduit or needle 27 in direction 30 towards concave side 103 of diaphragm 1 and passing through diaphragm 1 from volume 22 into volume 21. When conduit 27 passes through diaphragm 1 and remains in the engaged position shown in FIG. 3, compressive forces 24 and 25 force the surface of diaphragm 1 into sealing engagement with the external surface 28 of conduit 27. When plastic tube or conduit 27 is removed, forces 24 and 25 cause perforation 14 to close, again causing diaphragm 1 to provide a fluid-tight non-leaking surface.

FIGS. 5(a)–5(c) show the diaphragm assembly as a part of an intravenous bag 110, a syringe 111, and a medicament bottle 112.

In FIGS. 5(a)–5(c), the external surface 130 of conduit 15 is shown to have a protruding stop member 131 with an inclined surface 132 facing proximal conduit end 115 and a vertical surface 133 facing conduit distal end 120, completely encircling conduit 15. Stop member 131 is designed to mate with a locking mechanism such as that described in U.S. Pat. No. 5,221,272, the disclosure of which is incorporated herein by reference.

Figure 6:
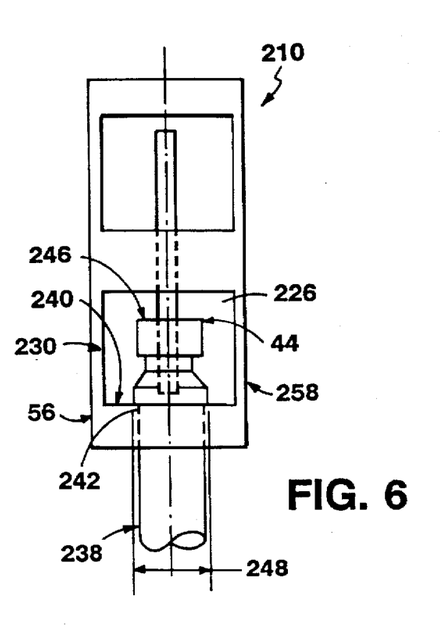
FIG. 6 illustrates a connector in an engaged position with the diaphragm assembly including a conduit.
Figure 7:
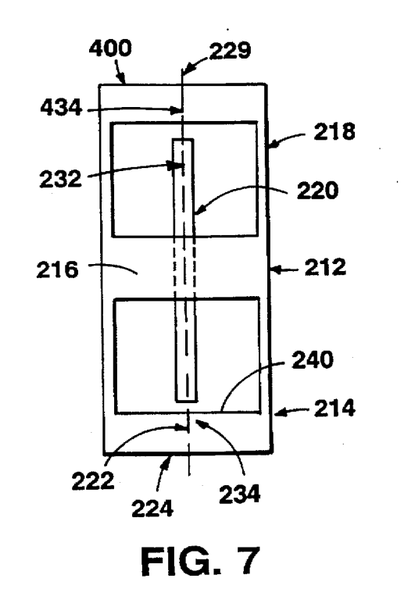
FIG. 7 illustrates a connector in an unengaged position with the diaphragm assembly.

Referring to FIGS. 6 and 7, the complete quick-connect coupling assembly 210 is shown comprising a quick-connect primary body 212 in an engaged position with a diaphragm assembly and conduit 238.

FIG. 7 shows the primary body 212 of the connector by itself without engagement with the diaphragm assembly conduit 238.

The primary body 212 of connector 210 is formed of a flexible retaining end portion 214, a non-flexible central portion 216, and an opposite end portion 218. A central hollow axial tubular structure 220, such as a needle, extends from a location 222 in proximity to the distal end 224 of flexible retaining end portion 214, through and along the longitudinal axis of primary body 212 to a location 434 in proximity to distal end 400 of flexible end portion 218. Tubular structure 220 is integral with the primary body at its central portion 216. An external wall 230 joins, supports and separates the flexible retaining end portion from the non-flexible central portion of the primary body by a fixed spacing distance, with two similar opposite openings 226 appearing in wall 230 as shown. Particular portions of wall 230 forming the connection between central portion 216 and end portion 214 are identified as side wall 256 and 258.

A similar and opposing end structure exists in opposite end portion 218 which is connected with and spaced a fixed distance from, central portion 216 by the same external wall 230. External wall 230 at this end also has two similar opposite openings 228 formed out of the wall.

Tubular structure 220 contains a central axial passageway 232 running lengthwise through the tubular structure and suitable for the transmission of fluid. The two end segments of tubular structure 220 consist of sharp, mildly sharp or blunt ends 234 suitable for puncturing a diaphragm made of latex or of other similar materials.

The relative positions of retaining member 214 and conduit 238 prior to, during, and after the insertion of conduit 238 into the primary body of the connector are next illustrated and explained with reference to FIGS. 8, 9, and 10, respectively.

Figure 8:
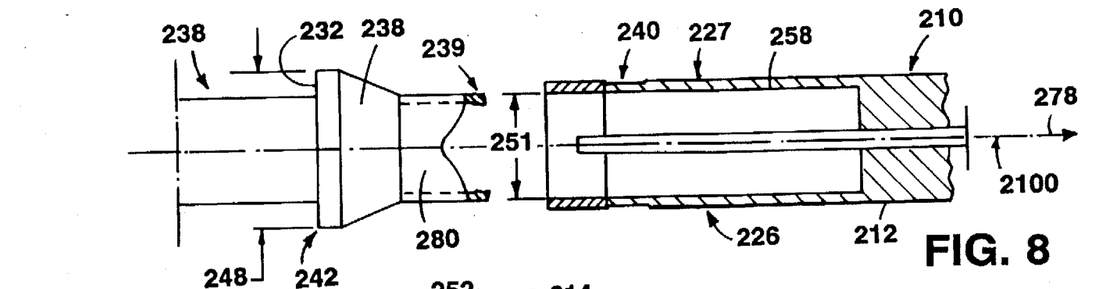
FIG. 8 illustrates the relative condition of the connector and the diaphragm assembly prior to insertion of the diaphragm assembly and conduit into the connector body.

In FIG. 8, connector 210 and conduit 238 are shown prior to insertion. Conduit 238 is pushed in a direction 278 and inserted into connector 210 with the central axis 280 of conduit 238 coinciding with the central axis 2100 of connector 210. End 244 of conduit 238 incorporates diaphragm 14.

Figure 9:
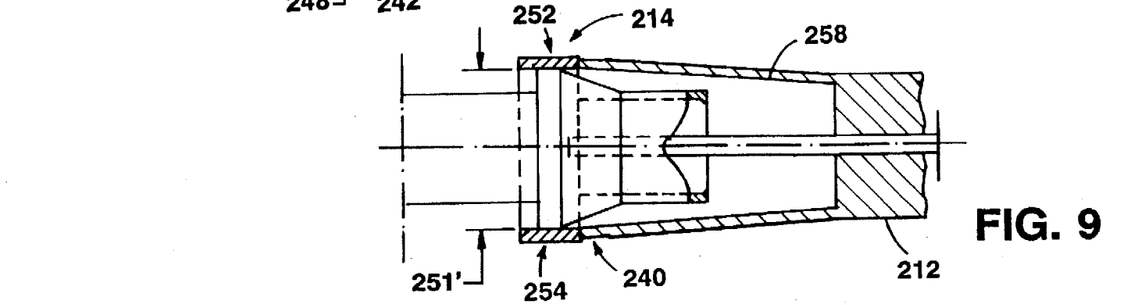
FIG. 9 illustrates the relative condition of the connector including the condition of the retaining member of the connector during insertion of the diaphragm assembly into the connector body.

FIG. 9 illustrates the two connector components during insertion where forces 264 and 262 are exerted upon wall 256 and 258, respectively, and walls 252 and 254 react by moving outward, such that the distance of interwall separation has increased from 251 to 251'. The distance 251' slightly exceeds the maximum diameter 248 of stop member 242, thereby permitting the stop member to pass through flexible retaining end portion 214. As the leading edge 239 of conduit 238 enters into flexible retaining end portion 214 and encounters the end 234 of tubular structure 220, diaphragm 14 incorporated in the leading edge of the conduit is pierced. As conduit 238 continues to be pushed in a direction 278 and into primary body 212, the trailing edge 282 of stop member 242 passes surface edge 240 of flexible retaining end portion 214 of the connector. When this occurs, forces 262 and 264 are removed and end portion 214 returns to the condition and shape as initially indicated in FIG. 8, prior to insertion.

Figure 10:
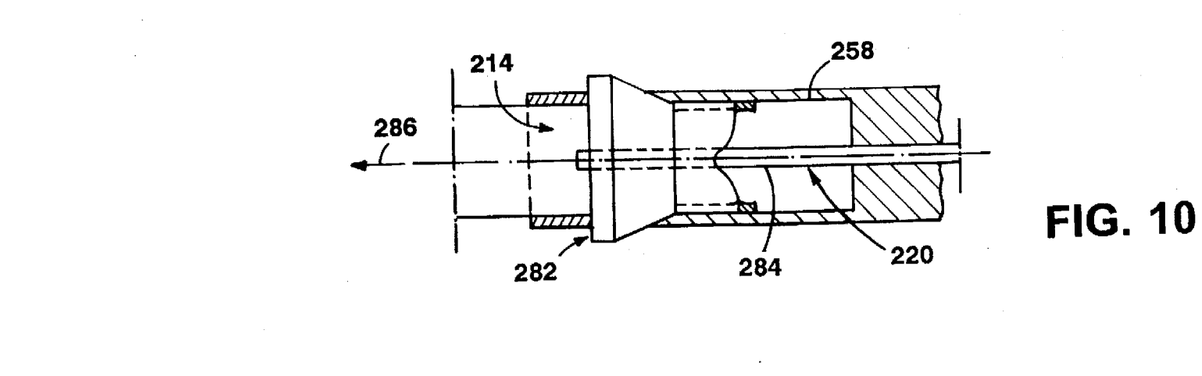
FIG. 10 illustrates the relative condition of the connector and diaphragm assembly after insertion of the diaphragm assembly/conduit into the connector body.

FIG. 10 shows that after insertion, connector edge 240 and stop member edge 282 abut and press firmly against each other so that conduit 238 is held securely in place and locked in primary body 212. A fluid tight leak proof seal has simultaneously been formed at 284 where diaphragm 1 encircles tubular structure 220.

Figure 11:
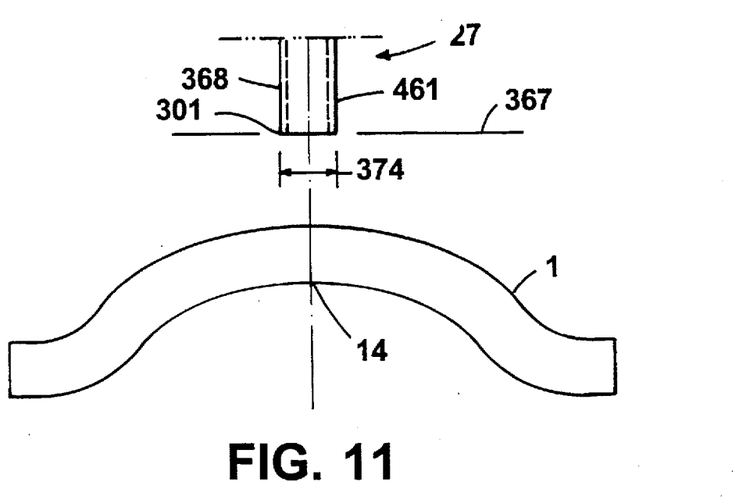
FIG. 11 is a partial sectional view of a perforated diaphragm in accordance with the invention as a blunt tipped needle approaches it.

An important aspect of this invention is illustrated in FIG. 11, the use of a blunt needle, tube or conduit 27 within connector 210. The use of a blunt needle is made possible by the pre-pierced diaphragm 1 of this invention. Only a gentle push of blunt needle 27 into the perforation 14 pre-formed in diaphragm 1 is required for operation. FIG. 11 shows blunt needle 27 and diaphragm 1 prior to the insertion of the blunt needle 27 into diaphragm 1. Although blunt needle 27 is contained within conduit 210 as shown in FIG. 6, only the blunt needle 27 itself is depicted in FIG. 11. The opening 301 of blunt needle 27 is contained within plane 367, which is substantially perpendicular to the outer surface 368 of blunt needle 27.

Figure 12:
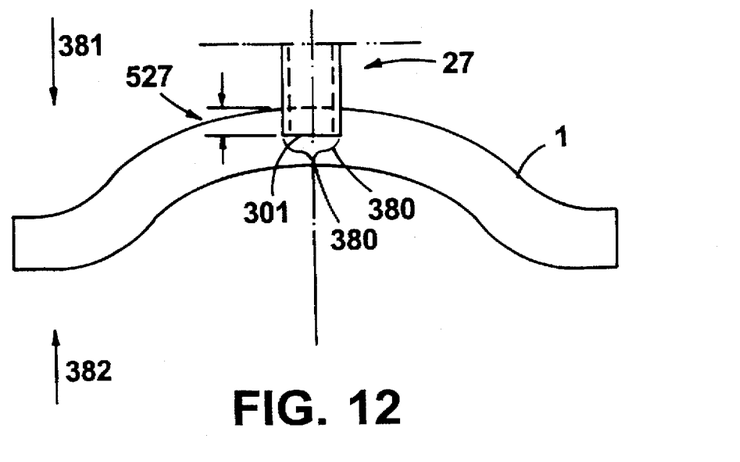
FIG. 12 depicts the entry of the blunt tipped needle of FIG. 11 into the perforation of the diaphragm.
Figure 13:
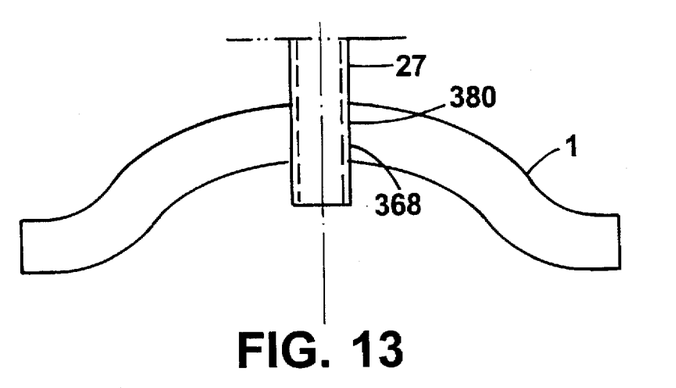
FIG. 13 depicts the blunt tipped needle of FIGS. 11 and 12 having penetrated completely through the perforated diaphragm.

FIG. 12 shows blunt-tipped needle 27 partially inserted into perforation 14 of diaphragm 1. Blunt leading edge 301 of needle 27 gently opens perforation 14 without cutting into surface 380 of the perforation. Needle 27 moves in the direction of arrow 381 during insertion and in the direction of arrow 382 during removal. During the insertion and withdrawal of needle 27 from diaphragm 1 the surfaces 380 of perforation 14 remain in sealing contact with the needle, preventing the leakage of fluids, air or foreign matter into or from the container or conduit sealed by diaphragm 1. As shown in FIG. 13, when needle 27 is fully inserted through the perforation 14 of diaphragm 1, the surface 380 of the perforation is everywhere tightly pressed against outer surface 368 of needle 27, forming a tight seal.

The outer diameter 374 of blunt needle 27 will range from approximately 0.080 to 0.12 in, the inner diameter 374 will range from 0.040 to 0.055 in. These dimensions will vary depending on the type of needle, tube or conduit employed in the particular application in which the assembly is employed.

Figure 14:
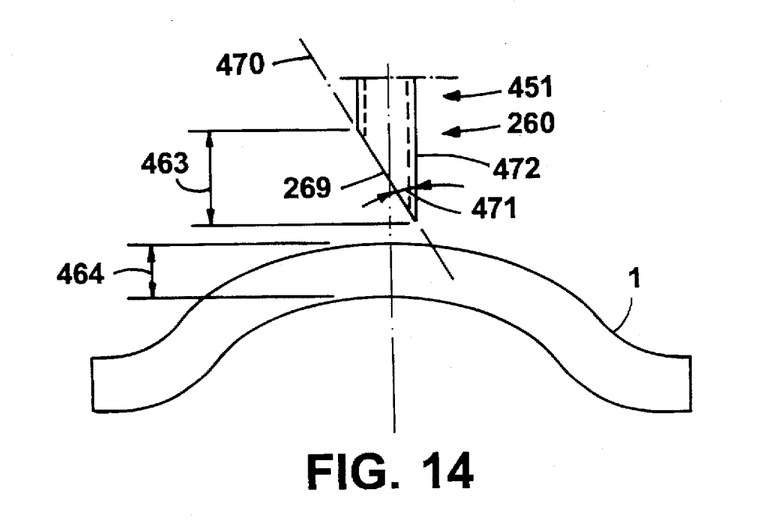
FIG. 14 is a view of a sharp tipped needle approaching the diaphragm of FIG. 11.

FIGS. 14–18 demonstrate the superiority of the combination of the blunt tipped needle and the pre-pierced diaphragm of this invention over conventional sharp needles used with the diaphragm assembly of this invention. FIG. 14 shows sharp-tipped needle 451 and diaphragm 1, prior to the insertion of needle 451 into diaphragm 1. Lead edge 401 of needle 451 is contained within plane 470, which makes an acute angle 471 with needle outer surface 472. In a blunt needle according to this invention, angle 471 is substantially equal to 90°.

Figure 15:
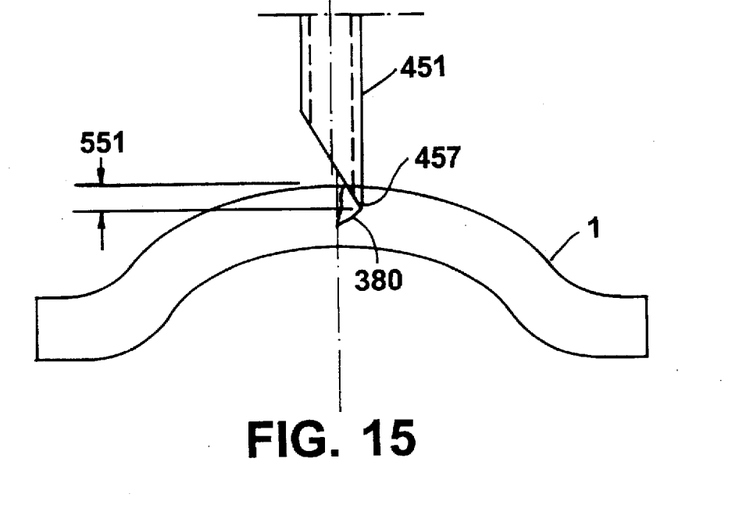
FIG. 15 depicts the entry of the sharp tipped needle of FIG. 14 partially into the diaphragm.
Figure 16:
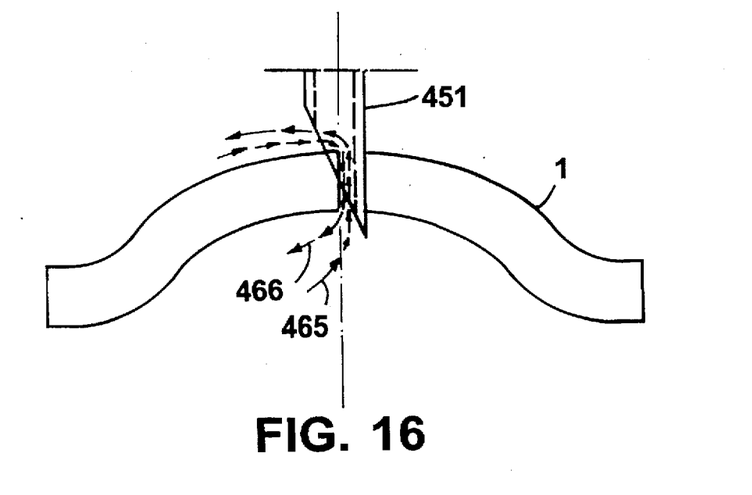
FIG. 16 depicts the further penetration of the sharp tipped needle of FIG. 16 into the diaphragm.
Figure 17:
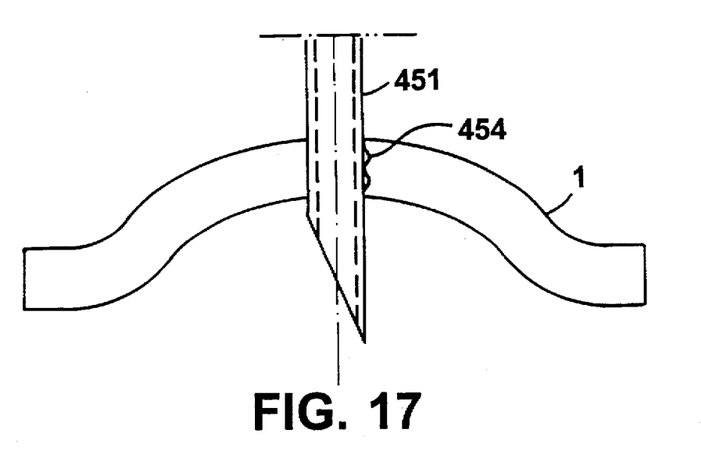
FIG. 17 depicts the diaphragm of the invention with the sharp tipped needle of FIGS. 14–16 having penetrated completely through the perforated diaphragm.
Figure 18:
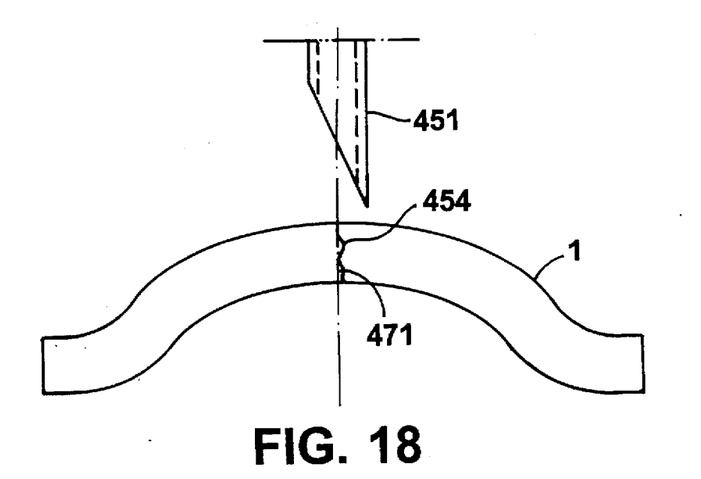
FIG. 18 shows the diaphragm of the invention with the sharp tipped needle of FIGS. 14–17 having been fully removed from the diaphragm.

FIG. 15 shows sharp-tipped needle 451 partially inserted into diaphragm 1, to approximately the same depth as shown in FIG. 12. FIG. 16 shows sharp-tipped needle 451 inserted further through diaphragm than FIG. 15, but not all the way through. FIG. 17 shows needle 451 fully inserted into the perforation in diaphragm 1 and passed through it. FIG. 18 shows needle 451 and diaphragm 1 after complete removal of the needle from the diaphragm.

As can be seen beginning in FIG. 15, the insertion of sharp-tipped needle 451 to depth 551 causes the leading edge 456 of the needle to cut into the perforation wall 380, thereby severing or lacerating a piece of diaphragm 1. In FIG. 12, by contrast, the leading edge of the blunt needle 27 slides past the wall 380 of the perforation without damaging the diaphragm.

FIG. 16 shows the additional damage caused by the sharp needle 451 as it continues into the perforation in the diaphragm. When the length of the forward edge 463 of the sharp needle 451 exceeds the thickness 464 of diaphragm 1, a two-way leak path 465, 466 exists as the needle is being inserted, allowing for blood or other fluid to leak into or from the container or conduit sealed by diaphragm 1. By contrast, blunt needle 27 shown in FIG. 12 has essentially no forward edge length, since its leading edge 301 lies in a plane perpendicular to the outer surface of the blunt needle, so no two-way leak can occur in a perforated diaphragm with a blunt needle.

FIG. 17 shows the residual effects of the damage caused by the use of a sharp needle. Even though the two-way leakage shown in FIG. 16 is not as significant a problem, there remains a pathway for leakage in the areas where material 454 has been removed from the perforation walls by the passage of the sharp needle. The removal or laceration of material diminishes the restorative force of the rubber of the diaphragm to fill the gaps between the wall of the perforation and the outer surface of the needle, thus allowing fluid, air and bacteria to leak through the perforation in the diaphragm. This means that once a sharp tipped needle has been used with the diaphragm assembly of this invention, the diaphragm is useless for resealing a container because of unacceptable leakage. This problem grows worse as the diaphragm is resealed again. FIGS. 12 and 13 show that no such problem exists when a blunt tipped needle is used; the diaphragm remains completely intact, thereby providing a resealing surface for a fluid container or conduit.

The diaphragm assembly of this invention in combination with the blunt tipped needle, tube or conduit disclosed herein is suitable for use with many conventional locking systems, as its external configuration may be adapted easily to mate with well-known commercially ports like the SAFSITE™, CLAVE™ and BAXTER™ ports. The modification is the same for each of these ports, namely, the addition of a stop member adapted for the given port such as stop member 131 shown in FIG. 5(a).

Figure 19:
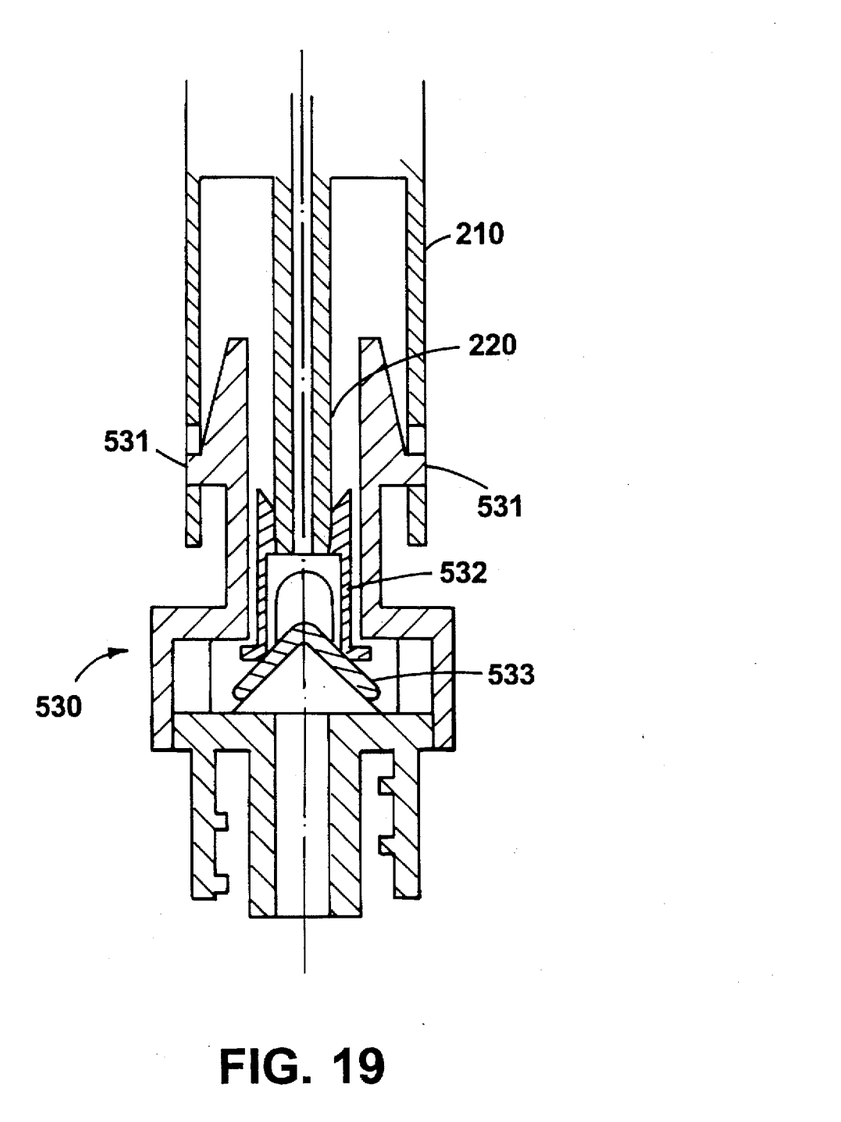
FIG. 19 shows the assembly of this invention in use with a modified commercially available port.

The SAFSITE port in use with the assembly of this invention is illustrated in FIG. 19. Connector 210 is shown in an engaged position with modified commercially available SAFSITE port 530. A blunt needle carrying tubular structure 220 makes contact with SAFSITE valve component 532 when connector 210 engages stop member 531, which has been added to the commercially available port. Valve component 532 presses upon membrane 533, permitting fluid flow. When connector 210 is disengage from port 530, membrane 533 returns to a closed position.

Figure 20:
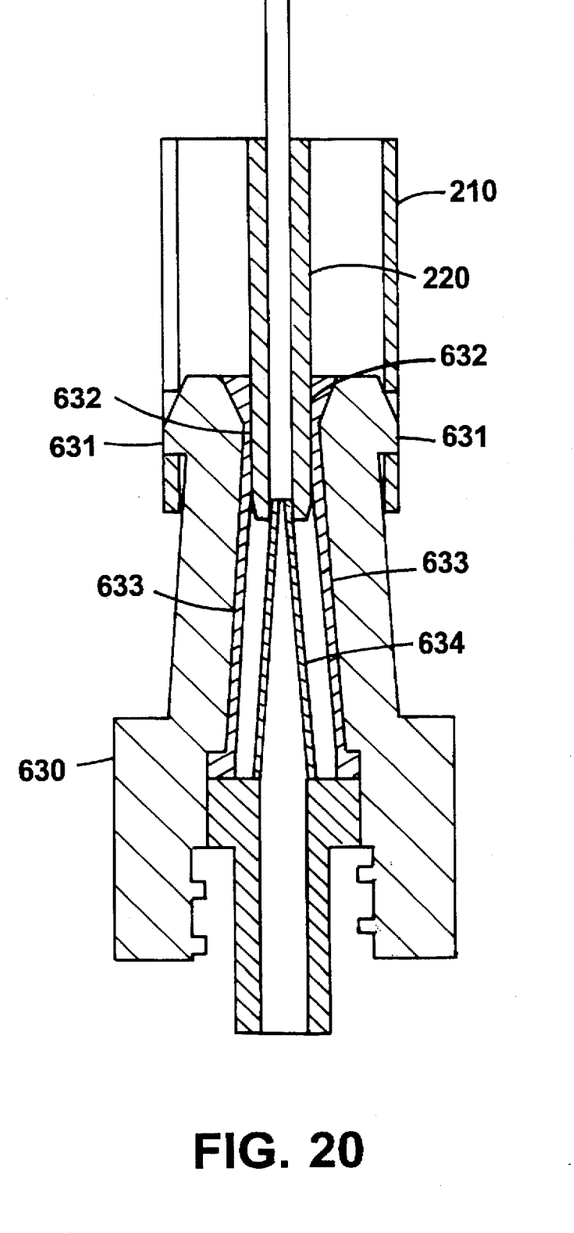
FIG. 20 shows the assembly of this invention in use with another modified commercially available port.

FIG. 20 shows the assembly of this invention in combination with a modified CLAVE port 630. Blunt needle tubular structure 220 enters port 630, forming a fluid-tight seal at 632 with port member 633. Conical port structure 634 enters into blunt needle structure 220, forming a fluid passageway when connector 210 engages with and locks stop member 631 which has been added to the commercially available CLAVE port. When connector 210 is disengaged, port sealing member 633 closes to form a fluid-tight seal.

Figure 21:
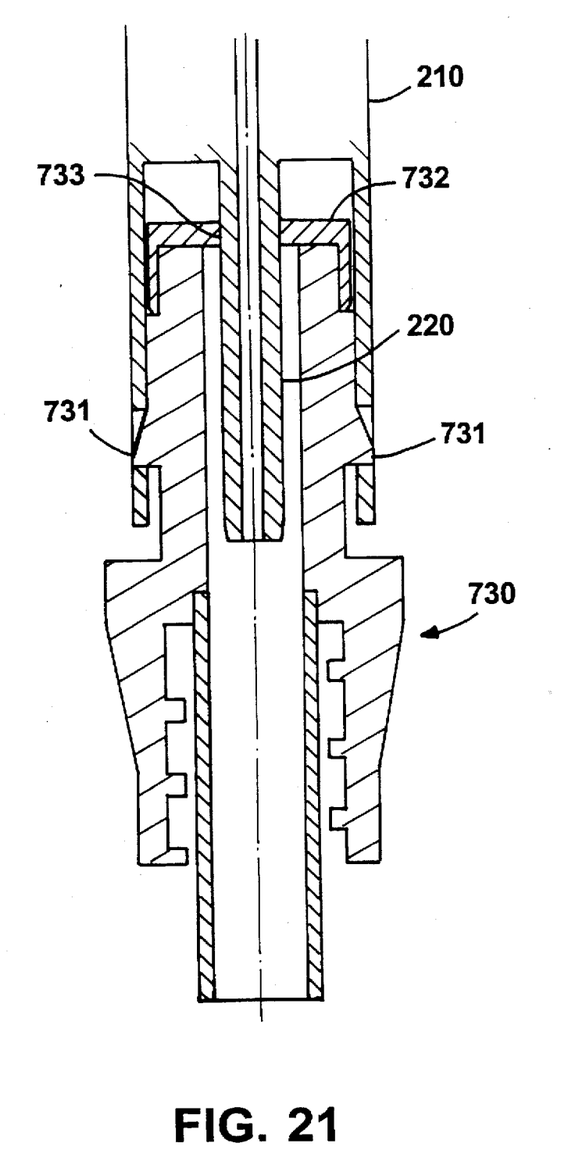
FIG. 21 shows the assembly of this invention in use with yet another modified commercially available port.

FIG. 21 shows the assembly of this invention in combination with a modified BAXTER port 730. Blunt needle tubular structure 220 enters port 730, forming a fluid-tight seal at 733. The blunt needle structure 220 passes through thick sealing diaphragm 732, forming a fluid passageway when connector 210 engages with and locks stop member 731 which has been added to the commercially available BAXTER port. When connector 210 is disengaged, diaphragm 733 closes to form a fluid-tight seal.

Figure 22:
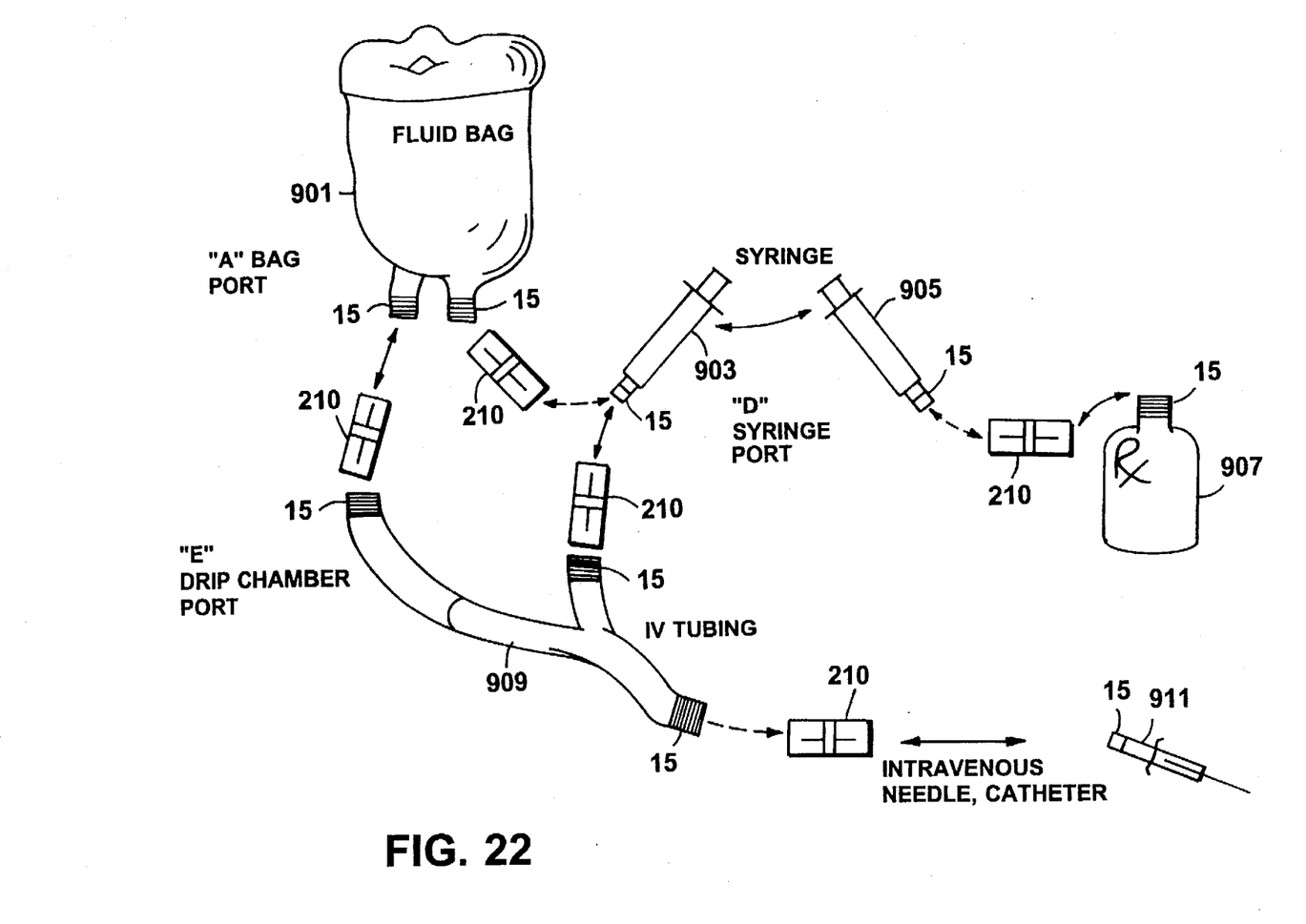
FIG. 22 shows a fully assembled unified fluid system according to this invention.

In the embodiment of FIG. 22, disclosing use of the diaphragm flow control assembly in a universal fluid delivery an control system, diaphragm flow control assembly port 100 containing diaphragm 1, is prepared by the manufacturer as fluid port 15 on any fa the components shown including bag 901, syringe 903, bottle 907, tubing 909 and catheter 911. The double male connector 210 of FIG. 7 could be carried in the pockets of the health care worker and used immediately on site to quickly and easily make any connection desirable among the various system components.

The diaphragm fluid flow control assembly of this invention works equally well if fluid port 15 is replaced with the SAFSITE®, CLAVE® or BAXTER® ports of FIGS. 19, 20 and 21, respectively. The double male connector 210 remains unchanged so that any combination of fluid port 15 or the SAFSITE®, CLAVE® or BAXTER® ports may be used with connector 210 within the universal fluid control and delivery system of FIG. 22.

Figures 23A, 23B:
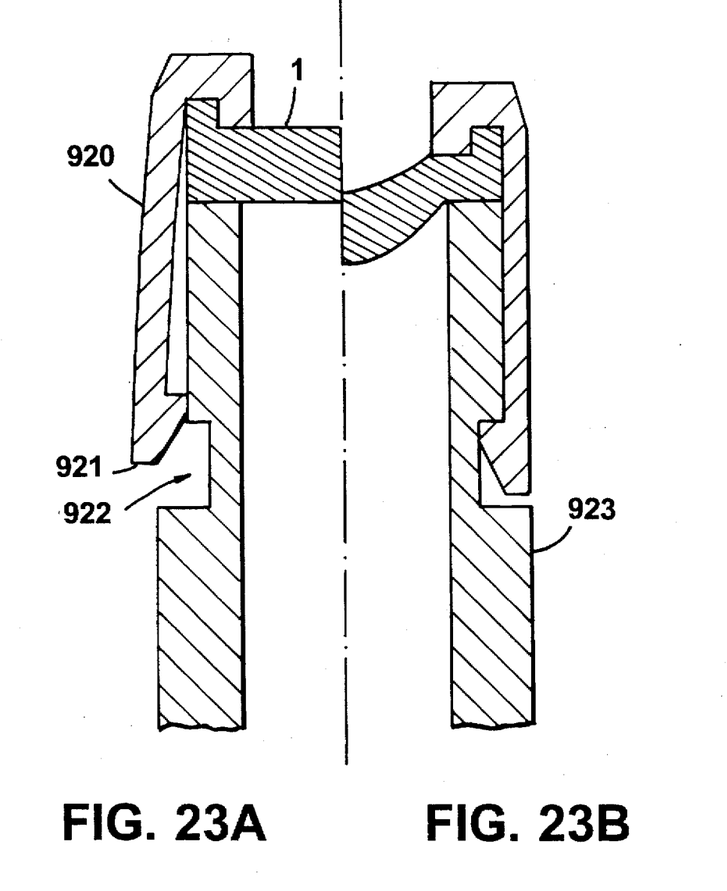

FIGS. 23(a) and 23(b) depict an alternative embodiment, in which diaphragm 1 is held in place by a plastic snap or cover 920 which when snapped into place causes diaphragm 1 to deform into a dome shape. FIG. 23(a) shows diaphragm 1 and plaster snap-on cover 920, end 921 of which snaps into groove 922 when pushed toward conduit 923. FIG. 23(b) shows diaphragm 1 formed into a coupler after plastic cover 920 has been snapped into place in groove 922.

Although the present invention has been fully described by way of example with reference to the accompanying drawings, it is to be understood that various changes and modifications will be apparent to those skilled in the art. Therefore, unless such changes depart from the spirit of the invention as defined by this specification and claims, they should be construed as being included herein.

What is claimed is:

1. A diaphragm fluid flow control assembly, comprising:
   a conduit having an elongated channel centrally disposed about a longitudinal axis and having a shoulder, located at a predetermined distance from an end of said conduit, protruding from an internal surface of said conduit and encircling the longitudinal axis;
   a perforated circular diaphragm disk having a preformed hole therethrough, which is inserted into said conduit and held in a position adjoining said shoulder within said conduit so that said diaphragm disk is squeezed against said shoulder along a periphery of said diaphragm disk so as to form a fluid-tight seal with said shoulder along the periphery of said diaphragm disk, said diaphragm disk having a diameter prior to insertion into said conduit greater than the largest internal diameter of said conduit;
   a ring, secured within said conduit and encircling the longitudinal axis, dimensioned so as to overlay the periphery of said diaphragm disk and squeeze the edge of said diaphragm disk against said shoulder of said conduit; and a tube or hollow needle having a cylindrical outer surface inserted through the pre-formed hole in said diaphragm disk, the opening of said tube or needle forming a plane substantially at a 90 degree angle to the outer surface of said tube or hollow needle, wherein the compressive forces cause the pre-formed hole in said diaphragm disk to form a fluid-tight sealing engagement with said tube or hollow needle inserted through said diaphragm disk.

2. A diaphragm assembly as claimed in claim 1, wherein a distal end of said conduit comprises a fluid reservoir.

3. A diaphragm assembly as claimed in claim 1, wherein said diaphragm disk assumes a dome shape having a convex side and a concave side when said diaphragm disk is inserted into said conduit and squeezed around the periphery by said ring, so that compressive forces are produced in said diaphragm disk directed toward the longitudinal axis forcing the pre-formed hole in said perforated diaphragm disk closed and forming a fluid-tight seal in said diaphragm disk.

4. A diaphragm assembly as claimed in claim 1, wherein said conduit comprises an external stop member, located at a distance from an end of said conduit, said stop member including an inclined surface facing toward said end and a rear surface facing another end of said conduit, encircling said longitudinal axis and configured to make mating engagement with a connector.

5. A diaphragm assembly as claimed in claim 1, wherein said tube or hollow needle is formed as an integral part of a connector designed to make a mating engagement with said conduit.

6. A diaphragm assembly as claimed in claim 1, wherein said conduit is internally dimensioned so as to form a seal about said tube or needle and permit fluid flow when mechanically locked to a connector dimensioned to mate with an external slip member encircling said conduit.

7. A medicament fluid storage, delivery and control system, comprising a fluid container portion comprising a plurality of fluid container components, each fluid container component having one or more openings for fluid entry or exit; a fluid transfer portion comprising a plurality of fluid transfer components, each fluid transfer component having one or more openings for fluid entry or exit; and a fluid control portion comprising a plurality of fluid flow control assemblies as claimed in claim 1, wherein said conduits are formed integrally with said openings in said fluid container components and in said fluid transfer components.

8. A medicament fluid storage, delivery and control system as claimed in claim 7, wherein the fluid container components are intravenous bags, prescription medication bottles or syringes.

9. A medicament fluid storage, delivery and control system as claimed in claim 7, wherein the fluid transfer components are tubes or catheters.

10. A diaphragm assembly as claimed in claim 7, wherein said connectors and conduits form leak free fluid flow paths when in mating engagement with said fluid conmtrol components or said fluid transfer components.

11. A diaphragm fluid flow control assembly, comprising:

a conduit having an elongated channel centrally disposed about a longitudinal axis and having a shoulder, located at a predetermined distance from an end of said conduit, protruding from an internal surface of said conduit and encircling the longitudinal axis;

a perforated circular diaphragm disk having a preformed hole therethrough, which is inserted into said conduit and held in a position adjoining said shoulder within said conduit so that said diaphragm disk is squeezed against said shoulder along a periphery of said diaphragm disk so as to form a fluid-tight seal with said shoulder along the periphery of said diaphragm disk, said diaphragm disk having a diameter prior to insertion into said conduit greater than the largest internal diameter of said conduit;

an encircling plastic snap member secured around said conduit and encircling the longitudinal axis, dimensioned so as to overlay the periphery of said diaphragm disk and squeeze the edge of said diaphragm disk against said shoulder of said conduit; and a tube or hollow needle having a cylindrical outer surface inserted through the pre-formed hold in said diaphragm disk, the opening of said tube or needle forming a plane substantially at a 90 degree angle to the outer surface of said tube or hollow needle, wherein the compressive forces cause the pre-formed hole in said diaphragm disk to form a fluid-tight sealing engagement with said tube or hollow needle inserted through said diaphragm disk.

* * * * *